United States Patent [19]

Bowman et al.

[11] Patent Number: 4,852,027

[45] Date of Patent: Jul. 25, 1989

[54] METHOD TO QUANTIFY THERMAL DISSIPATIVE MECHANISMS IN BIOMATERIALS

[75] Inventors: Harry F. Bowman, Needham; William H. Newman, Dedham, both of Mass.

[73] Assignee: Thermal Technologies, Inc., Cambridge, Mass.

[21] Appl. No.: 948,316

[22] Filed: Dec. 31, 1986

[51] Int. Cl.$^4$ .................. G01F 1/68; G06F 15/32
[52] U.S. Cl. ................... 364/557; 73/204.18; 128/630; 374/44; 374/169
[58] Field of Search ................. 364/557; 374/44, 25; 73/204; 128/691, 630, 632, 634

[56] References Cited

U.S. PATENT DOCUMENTS

| Re. 30,317 | 7/1980 | Lübbers et al. | 128/691 |
| 4,059,982 | 11/1977 | Bowman | 364/557 |
| 4,538,925 | 9/1985 | Zgonik | 364/557 |

OTHER PUBLICATIONS

Bowman et al., "Theory Measurement and Application of Thermal Properties of Biomaterials", *Annual Review of Biophysics and Bioengineering*, vol. 4, 1975, pp. 43–80.
H. F. Bowman, "Temperature Field Due to a Time Dependent Heat Source of Spherical Geometry in an Infinite Medium", Aug. 1974, pp. 296–299.
H. F. Bowman, "Estimation of Tissue Blood Flow", *Heat Transfer in Medicine*, Chapter 9, 1984.
Chato, "Method for the Measurement of the Thermal Properties of Biological Materials", 1976, pp. 16–25.

*Primary Examiner*—Felix D. Gruber
*Assistant Examiner*—Ellis B. Ramirez
*Attorney, Agent, or Firm*—Robert F. O'Connell

[57] ABSTRACT

A method for determining the properties of a medium by activating temperature changing means to change the temperature of the medium from a first unperturbed temperature to a second different temperature during a first time period and permitting the temperature to relax to a final unperturbed temperature during a second time period. In a particular embodiment, for example, the intrinsic thermal conductivity and diffusivity of the medium are calculated during a selected portion of the first time period assuming an arbitrary value for the perfusion, and the perfusion of the medium is calculated during a selected portion of the second time period using the calculated intrinsic thermal conductivity and diffusivity. The calculated perfusion is then used to recalculate the intrinsic thermal conductivity and diffusivity during the selected portion of the first time period and the perfusion is then recalculated using such recalculated intrinsic thermal conductivity and diffusivity. The recalculation steps are repeated until each of the recalculated values converge to a substantially non-changing value.

17 Claims, 3 Drawing Sheets

METHOD TO QUANTIFY THERMAL DISSIPATIVE MECHANISMS IN BIOMATERIALS

INTRODUCTION

This invention relates generally to techniques for determining the thermal properties of materials, as well as other properties related to or derived from such thermal properties, and, more particularly, to methods for determining primarily the thermal conductivity and thermal diffusivity of materials, in the presence or in the absence of fluid flow therein, and the monitoring and quantification of the flow rates of fluids flowing therein, i.e., perfusion in such materials as living tissues.

BACKGROUND OF THE INVENTION

A knowledge of the thermal properties of biomaterials has long been considered important to researchers and others interested in increasing man's understanding of the nature of materials and their thermal interactions, as well as to designers of equipment and systems in which the thermal characteristics of the materials used therein or operated thereon are of significance. For example, important information concerning biological materials, such as human and animal tissues, can be obtained from knowledge of the thermal properties thereof and of the perfusion characteristics of blood flowing therethrough.

Thus, it is known that biomaterials are capable of heat transfers by virtue of a temperature gradient, such heat transfer capability being especially important in living biomaterials because the state of life thereof, for example, may depend on the maintenance of a specific temperature level. Heat transfer by conduction is usually most important in determining the heat transfer within the biological medium and such heat transfer is best characterized in the steady-state by the thermal conductivity, k, of the medium and in the non-steady state by its thermal diffusivity, $\alpha$. Since there is no presently known method of determining k and $\alpha$ of a biomaterial from a knowledge of some other fundamental property or properties thereof, it is necessary to devise appropriate processes and apparatus to measure k and $\alpha$ in some appropriate manner.

Furthermore, there has been an increasing utilization, particularly in medical research and clinical laboratories, of processes which require heat transfer through biological materials, such as in cryobiology (e.g., cryosurgery), in tissue and organ preservation, in laser-tissue thermal interactions and in the use of thermal therapy for cancer treatment, for example, all of which require a knowledge of such thermal properties for the intelligent use of these processes. Other procedure which are heat transfer dependent and, thus, require a knowledge of thermal properties include clinical applications of ultrasonic wave energy, microwave energy and laser beam energy in both diagnostic and therapeutic operating modes.

Such processes require more extensive and more reliable information concerning the thermophysical properties of such materials and, in particular, information concerning the thermal conductivities, thermal diffusivities and the flow rates of fluids (perfusion) through the biological medium, which information permits the determination of temperature distributions and heat transfer rates. It is particularly important, for example, to monitor the flow rate of blood through tissue so that flow disturbances can be monitored and corrective action taken in cases where maldistribution of blood flow in a patient would have unfavorable and possibly fatal consequences.

Techniques which have been applied to the measurement to properties of biological materials have included both invasive and non-invasive techniques. General summaries of such techniques and the limitations thereof are presented in the text, Annual Review of Biophysics and Bioengineering, "Theory, Measurement and Application of Thermal Properties of Biomaterials," H. Frederick Bowman et al., pp. 43–80, Vol. 4, 1975 and in the text, *Heat Transfer in Medicine and Biology*, Vol. 1, Edited by A. Shitzer and R. C. Eberhart, "Estimation of Tissue Blood Flow" H. Frederick Bowman, Chapter 9, pp. 193–229, Plenum Publishing Corp. 1984. Still further background information is contained in U.S. Pat. No. 4,059,982 issued to H. F. Bowman on Nov. 29, 1977 as well as in the description of the invention contained therein.

In accordance with the invention described in the aforesaid Bowman patent, a particular thermal model is developed and a particular implementation of the solution of the heat conduction equations utilizing a thermistor probe is described for providing a realistic representation of the thermal properties of the thermistor bead and the surrounding medium so as to produce an accurate measurement of such properties as thermal conductivity and thermal diffusivity from which other thermal properties and states of flow can be derived. In accordance therewith the thermistor bead of the probe is treated as a distributed thermal mass and the heat conduction equation is solved for both the interior of the bead as well as the region of the medium surrounding it.

The thermistor bead is placed in a medium and the bead and the region of the medium surrounding it assume an initial equilibrium, or reference, temperature. The temperature of the bead is raised to a predetermined level above the equilibrium temperature by applying electrical energy to the bead which thereupon thermally dissipates in the bead and its surrounding medium, thereby raising the temperature of the surrounding medium. If the temperature rise in the bead is to be maintained at the desired level, the electrical energy must be dissipated at a rate which is sufficient to maintain the temperature at the desired level and the electrical power required for such purpose depends on the heat transfer characteristics of the surrounding medium. Thus, if the characteristics of the medium are such as to enhance the heat transfer, a greater number of electrical power will be needed to maintain the desired temperature increment between the reference temperature and the temperature at the desired predetermined level, while, if the characteristics thereof are such as to impede heat transfer, less electrical power will be needed to maintain the temperature increment.

In a biological medium such as human or animal tissue, for example, the heat transfer capability of the medium depends upon the intrinsic thermal conductivity of the medium, the local blood flow rate in the medium and the specific heat of the blood therein, such characteristics contributing to a property which, for convenience, can be referred to as the "effective thermal conductivity" of the medium. Such term can be defined as a measure of the rate at which heat is being removed from the bead by (or transported through) a medium in the presence of fluid flow in the medium.

Such property can be contrasted with the "intrinsic thermal conductivity" thereof which can be defined as a measure of the rate at which heat can be removed from the bead for a given temperature gradient by (or transported through) a medium in the absence of any fluid flow therein (e.g., a biologic medium in which no blood flow is present).

The initial reference temperature of the bead and medium is determined and power is applied thereto to raise the mean temperature of the bead to a fixed predetermined level and is maintained at a desired, constant level above the reference temperature.

A data processor is used to calculate both the thermal conductivity and the thermal diffusivity of the medium in accordance with expressions derived from solutions to the transient heat diffusion equations both for the interior of the bead and for the surrounding region of the medium, arrived at by using a thermal model which takes into account the distributed thermal mass of the thermistor bead and the thermal characteristics of the surrounding medium.

The flow rate of a fluid which moves through the medium (e.g., the flow rate of blood through a biologic medium) can be calculated in accordance with an expression also derived from solutions to the heat conduction equations which specifically include blood flow (perfusion) as a variable in such a thermal model representation. In order to utilize the heat conduction equations in such a system, the intrinsic thermal conductivity and thermal diffusivity must be determined under no flow conditions (i.e., in the absence of fluid flow). It is in some cases extremely difficult or substantially impossible to make such measurements in living organisms and it has been found necessary to resort to techniques which provide only approximations to such no flow conditions, so that the values used for the intrinsic conductivity and diffusivity involved produce inaccuracies in the calculations of the effective values thereof and of the perfusion values under flow conditions.

Moreover, it is helpful to provide a system in which the temperature and power characteristics are permitted to be controlled in a more flexible manner than in the invention described in the above Bowman patent which normally requires that the power characteristics be such that the bead volume mean temperature be maintained at a specified value, i.e., the value of $V_b$ be kept substantially constant. Further, while the aforesaid Bowman system permits reasonably accurate measurements of perfusion above certain relatively high perfusion levels, it becomes less accurate at relatively lower perfusion levels.

BRIEF SUMMARY OF THE INVENTION

The invention utilizes a technique for determining thermal conductivity and thermal diffusivity, as well as the perfusion characteristics of a perfused medium, in a manner which does not require any measurements under no flow conditions. Moreover, such technique is not restricted to maintaining the bead volume mean temperature at a value at which the change thereof from a reference temperature (i.e., $\Delta T$) is kept substantially constant. Further, the technique permits measurements to be made under effectively transient conditions, i.e., at times which are short relative to the time required for the system to reach steady state.

In accordance therewith, first of all, the temperature change produced in the medium is permitted by vary in any arbitrarily selected manner with time. Both the power required to heat the medium and the resulting temperature change is recorded. At least one selected intrinsic thermal property of the medium, e.g., the intrinsic thermal conductivity and/or thermal diffusivity thereof, is calculated using data obtained at a first time period. The perfusion of the medium is separately calculated using data obtained at a second time period and such at least one calculated intrinsic thermal property, the effects of the flow of the medium during the second time period being greater than the effects of the flow of the medium during the first time period.

In a particular embodiment, for example, equations are derived for a thermal model which requires at least one series of experimental measurements under flow conditions, such data obtained at selected times which can occur during a temperature change of a medium from a first unperturbed temperature to a second temperature as well as during a relaxation of the temperature of the medium from the second temperature back to an unperturbed value. As long as the data utilized include measurements made at at least two selected time periods in the overall temperature changing cycle, such equations can be used in an interactive data processing operation so as to converge relatively rapidly to a final solution for the conductivity, diffusivity and perfusion values that are desired. In one preferred embodiment, for example, the medium can be heated from an unperturbed temperature value to a second higher temperature value and then permitted to decay, i.e. to cool, to an unperturbed value. Measurements can be made which include at least two selected time periods, one during the heating portion of the cycle, for example, and one during the cooling portion thereof, for example, In such embodiment the effects of the medium flow on the measurements involved are greater during the cooling portion than during the heating portion of the cycle. In another embodiment, to improve the accuracy thereof, measurements can be made which include three separate selected time periods (e.g. two during the heating portion and one during the cooling portion) to provide the ability to simultaneously quantify thermal properties and perfusion over a wide range of perfusion levels and particularly at low perfusion levels.

Such measurements do not depend on maintaining the volume mean temperature of the medium so as to provide a constant $\Delta T$ with time and, in a heating/cooling cycle, power can be applied in any appropriate manner which produces any arbitrarily selected change in the volume mean temperature of the medium as a function of time.

DESCRIPTION OF THE INVENTION

The invention can be described in more detail with the help of the accompanying drawings wherein.

Figure 4:
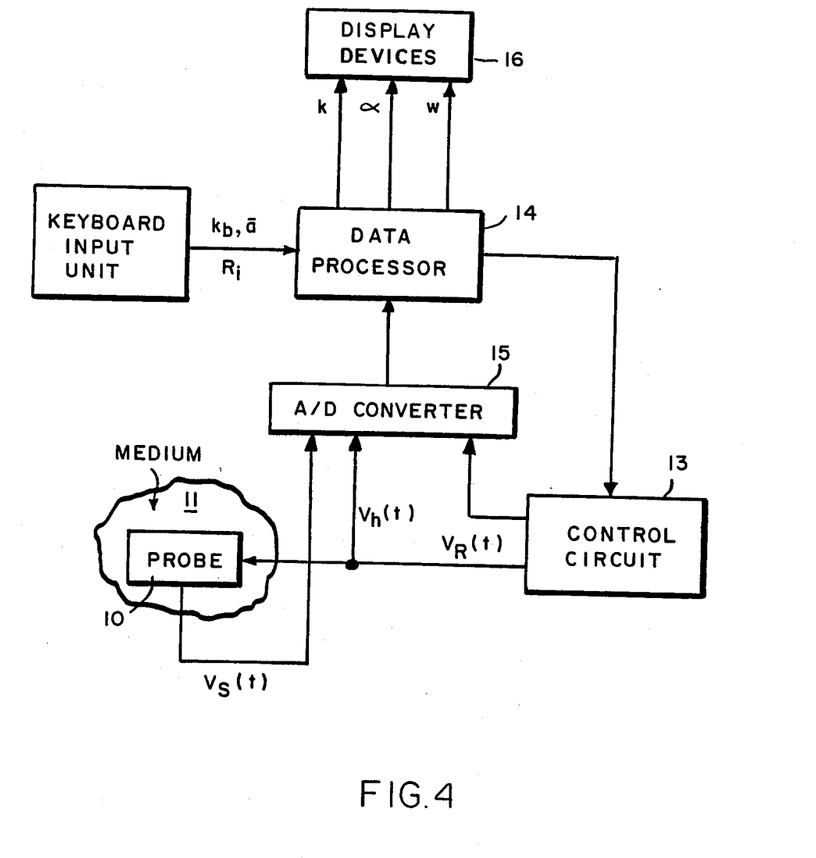
FIG. 4 shows a block diagram of an embodiment of a system in which the invention is used.

The techniques of the invention can be specifically implemented by use of a system such as shown in FIG. 4 which figure is substantially the same as that shown by the block diagram, identified as FIG. 1 in the aforesaid Bowman U.S. Pat. No. 4,059,982. As explained in such patent, a probe 10 is immersed in a medium 11 and can be heated by a heater voltage $V_h(t)$ supplied via control circuit 13. The sensed voltage $V_s(t)$ from probe 10 is supplied to A/D converter 15 for supplying to a data processor 14 in digital form for suitable processing thereof in order to determine k, $\alpha$, and w, the values of which can be displayed in a display device 16. The values of probe calibration constants $k_b$, $\bar{a}$, and $R_i$ can be supplied by a user via a suitable keyboard input unit. Such operation is essentially described in the aforesaid Bowman patent for a particular mathematical model described therein and the same system as generally depicted therein can also be used for a different mathematical model, the processiing equations required to be implemented in data processor 14 being different depending on the mathematical model selected.

Accordingly, in order to understand the techniques of the invention it is helpful to describe, first of all, a mathematical model which is used to derive typical equations for use in determining the thermal properties which are desired. Once such equations are derived, the solutions thereof can be readily implemented thereof in a data processor 14 using skills well known to the data processing art.

For example, the temperature fields of a finite, heated thermistor bead (probe), and a homogeneous, infinite, perfused medium, in which the bead is placed can be described by a coupled thermal model as follows:

$$\text{Bead: } \rho_b c_b \frac{\partial T_b}{\partial t} = k_b \nabla^2 T_b + \Gamma + \beta f(t) \tag{1}$$

$$\text{Medium: } \rho_m c_m \frac{\partial T_m}{\partial t} = k_m \nabla^2 T_m - \lambda^2 k_m T_m \tag{2}$$

Equation (2) is derived from the full, bioheat transfer equation for heat transfer in perfused biological tissue. This equation is described more fully in the publication "Heat Transfer Mechanisms and Thermal Dosimetry" by H. F. Bowman, Jour. Nat. Cancer Inst., Monograph 61, Vol. 60, 1981, pp. 437–445.

In Equation (2) it is assumed that tissue metabolic heat generation and perfusion do not change materially over the duration of the transient measurement procedure. The temperature, T, is the temperature elevation (or depression) produced by the measurement procedure and the applied power, $\Gamma + \beta(t)$ is such as to produce the required tissue heating (or cooling), as measured from the non-perturbed, initial probe-tissue equilibrium state. In the above equation the subscripts b and m refer, respectively, to bead (probe) and medium (tissue) properties, T is temperature, k is thermal conductivity, $\alpha$ is thermal diffusivity, $\lambda$ is the perfusion parameter, $\sqrt{wc_f/k_m}$, where w is the perfusion and $c_f$ is the specific heat of a fluid flowing therein, c is volumetric heat capacity, and $\Gamma$ and $\beta f(t)$ are discussed below. The coupled system of a second-order, partial differential equation requires two initial conditions and four boundary conditions as follows:

Initial Conditions ($t = 0$)

$T_b = 0 \quad T_m = 0$

Boundary Conditions ($t \geq 0$)

For $r = 0 \quad \frac{\partial T_b}{\partial r} = 0$

For $r = r_{bead} \quad T_b = T_m, \quad k_b \frac{\partial T_b}{\partial n} + k_m \frac{\partial T_m}{\partial n} = 0$ For $r \rightarrow \infty \quad T_m \rightarrow 0$ where $\bar{r}$ is a coordinate position, and n represents the outwardly directed normal to the bead-medium interface.

Exemplary solutions to the above coupled, perfused conduction equations in accordance with the invention may be considered with reference to a bead which has a spherical configuration. Other solutions can be determined by those in the art for other configurations, such as a cylindrical bead, an ellipsoidal bead, etc,. For a spherical bead having a radius a, the following experimental procedure, or protocol, can be considered:

(1) a heating of the bead to provide a volume averaged constant temperature change, $\Delta T$, which takes into account both, the bead and the medium geometric and thermal properties. This solution is represented by $$P(t) = \frac{4\pi a k_m \Delta T}{\frac{1}{5\gamma} + \frac{1}{1+\lambda a}} \left[ 1 + \frac{\frac{a}{\sqrt{\pi \alpha_m}} f(t)}{\frac{1-\lambda^2 a^2}{5\gamma} + 1 + \lambda a} \right] \tag{3}$$

$$V_b = \Delta T$$

where $V_b$ is the bead volume mean temperature, i.e., $$V_b = \frac{1}{\gamma_b} \int_{\gamma_b} T_b \, d\gamma$$

where P is the power required to heat the bead, and $\gamma = k_b/k_m$, and $\gamma_b$ is the bead volume.

(2) cooling of the bead following shut-off of power after heating the bead to a constant temperature, which also takes into account both the bead and the medium geometric and thermal properties. This solution is represented by $$P = 0 \tag{4}$$

and

-continued $$\frac{V_b(t)}{\Delta T} = \frac{a/\sqrt{\pi \alpha_m}}{\frac{1-\lambda^2 a^2}{5\gamma} + 1 - \lambda a} \left[ \{f(t - t_{heat}) - f(t)\} + \frac{a/\sqrt{\pi \alpha_m}}{\frac{1-\lambda^2 a^2}{5\gamma} + 1 + \lambda a} \cdot \frac{\sqrt{t_{heat}}\, e^{-\lambda^2 \alpha_m t}}{t\sqrt{t - t_{heat}}} \right]$$

where $t_{heat}$ is the time over which heating is supplied.

Another experimental procedure which can be considered is the following:

(3) heating of the bead at constant power, Po, which also takes into account both the bead and medium geometric and thermal properties. This solution is represented by $$P = Po \quad (5)$$

and $$V_b(t) = \frac{P_o}{4\pi a k_m} \left[ \frac{1}{5\gamma} + \frac{1}{1 + \lambda a} - \frac{a/\sqrt{\pi \alpha_m}}{1 - \lambda^2 a^2} f(t) \right]$$

(4) cooling of the bead following shut-off of power after heating at constant power, which also takes into account both the bead and medium geometric and thermal properties. This solution is represented by $$P = 0 \quad (6)$$

$$V_b(t) = \frac{P_o}{4\pi k_m \sqrt{\pi \alpha_m}} \cdot \frac{1}{1 - \lambda^2 a^2} [f(t - t_{heat}) - f(t)]$$

The above expressions for the applied heating power P(t) may be presented in the form of $\Gamma + \beta(t)$, which terms represented, respectively, the constant (or steady-state) power term and a transient power term used to maintain the temperature elevation $\Delta T$.

In general, a function f(t) is derived which is a characteristics transient function determining either (1) the heating power for providing a constant temperature increment, (2) the temperature, when heating at a constant power, (3) the temperature during the delay following the shut-off of heating power at either a constant power or a constant temperature increment, or (4) the temperature for any arbitrary heating procedure. While derived solutions are valid for bead and medium heating according to any arbitrary experimental, or measurement, protocol, the above solutions are specifically presented for the cases of heating at constant temperature increment, at constant power, and for the subsequent cooling following power shut-off for a spherical bead. In each of the cases considered above it is confirmed that the characteristic function for the problem, whether for power required during bead hating or temperature during the decay, is given by the function f(t).

For a spherical bead in a non-perfused medium it has been shown in the above Bowman patent that the function f(t) approaches the representation, in the limit of longer heating time, of $$f(t) = 1/\sqrt{t}$$

A theoretical result of the analytical solution of the combined heating and cooling problem is to provide a derivation of an expanded f(t) in a non-perfused medium using a spherical bead. Such solution in such an embodiment is represented by $$f(t) = \quad (7)$$

$$\frac{\sqrt{\pi \alpha_m}}{a} (5\gamma + 1) e^{(5\gamma+1)^2 \alpha_m t/a^2} \, erfc\left[ (5\gamma + 1) \frac{\sqrt{\alpha_m t}}{a} \right]$$

where a is the bead (probe) radius, $\alpha$ is the thermal diffusivity of the medium, and $\gamma$ is the ratio $(k_b/k_m)$ of bead to medium thermal conductivity. This above form was derived by a solution of the heating problem for a spherical bead and it can be verified that this above expanded form of f(t) reduces to the previous case for long time periods (t is relatively large), or for a small bead (small radius a), and for a highly thermally conductive probe ($\gamma$ is large). It is also found that the above representation of f(t) describes bead heating power at shorter time periods than the $1/\sqrt{t}$ formulation, although requiring greater computational complexity.

It has further been found that such more accurate derivation for the function f(t) permits a more accurate determination of intrinsic thermal conductivity and diffusivity to be obtained early in the bead heating portion of a heating/cooling cycle, before the effect of perfusion becomes significant. Later in the heating portion, when the effect of perfusion is more pronounced, the contribution of perfusion to tissue heat transfer can then be more precisely identified and separated from the contribution due to conduction. Moreover, the above function f(t) permits greater accuracy in the measurement of tissue conduction and thereby permits a reduction in the duration of the experimental procedure, while maintaining the same measurement accuracy in perfusion. While the f(t) expansion presented above applies to a non-perfused medium, a complementary, expanded form of f(t) which takes into account perfusion can also be derived as follows:

$$f(t) = \frac{\sqrt{\pi \alpha_m}}{a} (5\gamma + 1) e^{-\lambda^2 \alpha_m t} e^{(5\gamma+1)^2 \alpha_m t/a^2} \, erfc\left[ (5\gamma + 1) \frac{\sqrt{\alpha_m t}}{a} \right] - \sqrt{\pi \lambda^2 \alpha_m} \, erfc \sqrt{\lambda^2 \alpha_m t} \quad (8)$$

The above mathematical model describes the heat transfer processes occurring both within the tissue and those occurring between the tissue and the thermistor probe, and is not limited to the requirement that the thermistor probe be heated to a constant temperature increment, as with the prior Bowman patent. The solution derived here considers the effect of finite bead size and bead properties during both bead heating and cooling, for both steady-state and transient heat transfer, as well as the effects of tissue thermal conductivity, thermal diffusivity and perfusion.

Given the above mathematical model for the thermal response of a heated thermistor bead placed in a perfused medium for both bead and tissue heating and the subsequent cooling thereof following power shut-off, certain procedures can be used in accordance with the invention in order to allow data taken during the heating portion of an experiment as well as during a subsequent temperature decay portion thereof to be analyzed for medium properties, including perfusion, and to allow the tissue properties of conductivity, diffusivity, and perfusion to be simultaneously obtained in a single experiment, without the need for an experiment under now flow conditions as in the prior Bowman patent.

Two examples of experimental procedures which can be used in accordance with the above embodiment of the invention can be discussed. First, a heating experiment can be performed in which bead heating power is applied for a selected time period so as to maintain the volume mean temperature of the bead at a constant increment above its initial baseline value. Second, the same experimental procedure can be performed in which temperature data is collected as well during the temperature decay time following power shut-off. In each case three tissue properties are to be determined, i.e., tissue thermal conductivity, tissue thermal diffusivity, and perfusion. For each experimental procedure data reduction algorithms as discussed below can be used to extract these properties from the experimental data. While bead heating at constant temperature can be used, and is specifically discussed below, it should be understood that nearly identical procedures can be used to analyze the data from an experiment where bead temperature is measured during heating at constant power and during the subsequent temperature decay following power shut-off. Procedures using identical principles may be developed to analyze the experimental data from any other arbitrarily selected heating-/cooling protocols, e.g., ramp or periodic power protocols.

Figure 1:
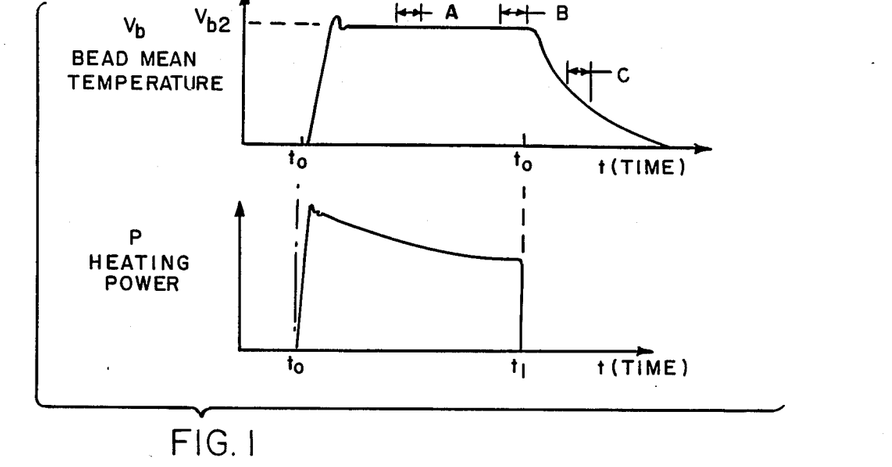
FIG. 1 depicts curves of bead volume mean temperature and power as a function of time with reference to a particular embodiment of the invention.

The times at which the above experimental algorithms can be implemented are illustrated in an exemplary manner in FIG. 1 wherein graphical representations are presented by the volume mean temperature $V_b$ b of the bead (probe) and of the heating power P applied thereto, both as functions of time. In the particular procedure illustrated therein, the power P is applied to $t_0$ in a manner such that the bead volume mean temperature $V_b$ rapidly reaches a selected level $V_b2$ and is maintained at such level for a selected time period until $t_1$, for example, at which time the power is reduced to zero (shut-off) and the temperature $V_b$ decays toward zero in a general manner as shown.

Approximation algorithms, as discussed below, can be used with data derived from measurements taken at different times during the overall heating/cooling cycle as, for example, early in the heating portion thereof with the time range or time window, illustrated by "A" in FIG. 1, later in the heating portion at "B", and during the cooling portion at "C".

Data taken during time window "A" is dominated by tissue conduction and the effects of the flow of the medium are relatively low. Data taken during the time window "B", occurring later in time as heating continues, is influenced to a greater extent by perfusion, i.e., the effects of the flow of the medium are greater than at time window "A".

One exemplary data analysis algorithm usable at time windows "A" and "B" consists of the following steps:

(1) calculate the intrinsic thermal conductivity and thermal diffusivity during time window "A" assuming an arbitrary value of perfusion by fitting the measured bead heating power vs time data during time window "A" to Equation (3), e.g. assume perfusion is zero;

(2) using such calculations of intrinsic thermal conductivity, and diffusivity, calculate perfusion during the window "B" by fitting the measured bead heating power vs. time data during time window "B" to Equation (3);

(3) using such calculated value for perfusion, recalculate the intrinsic thermal conductivity and diffusivity during time window "A" by fitting the measured bead heating power vs. time data during time window "A" to Equation (3);

(4) using such recalculations for intrinsic thermal conductivity and diffusivity, recalculate perfusion during time window "B" by fitting the measured bead heating power vs. time data during time window "B" to Equation (3);

(5) repeat steps (3), (4) until convergence to substantially non-changing intrinsic thermal conductivity and thermal diffusivity values and a substantially non-changing perfusion value is achieved.

Figure 5:
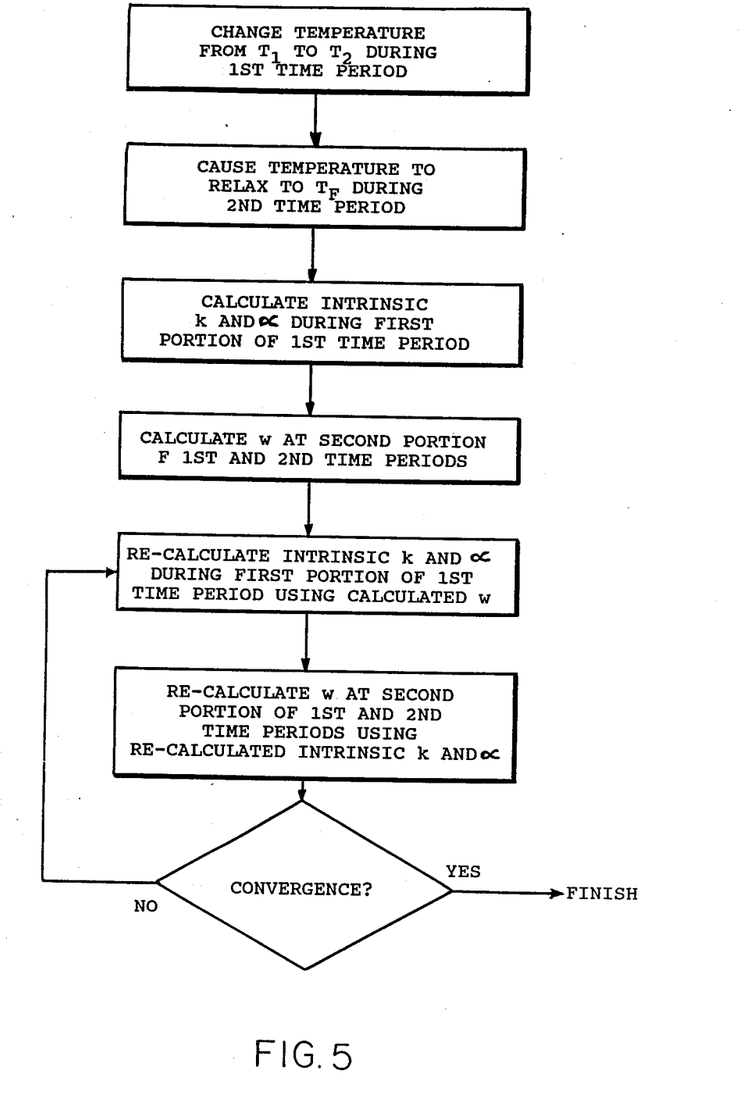
FIG. 5 shows a flow chart depicting an exemplary embodiment of the method of the invention.

FIG. 5 illustrates a low chart showing one particular exenokart enbodiment of the method of the invention as described above.

While the above algorithm is described as usuable at time windows "A" and "B" of FIG. 1, such algorithm can also be used, for example, with reference instead of time windows "A" and "C", wherein the measured bead mean temperature data would be fitted to Equation (4) within time window "C" which occurs during the cooling portion of the procedure. As above, the effects of the flow of the medium during the time window "C" are greater than during time window "A".

As a further alternative in order to produce even better accuracy, calculations with respect to three time windows "A", "B" and "C" can also be made in accordance with the following exemplary algorithm;

(1) calculate an estimated value of the intrinsic thermal conductivity and diffusivity during time window "A" assuming an arbitrary value of perfusion by fitting the measured bead heating power vs. time data during time window "A" to Equation (3), e.g. assume perfusion is zero;

(2) using the calculations of intrinsic thermal conductivity and diffusivity, calculate an estimate of the perfusion during time window "B" by fitting the measured bead heating power vs. time data during time window "B" to Equation (3);

(3) using the calculations of the thermal conductivity and diffusivity as calculated during time window "A" and the estimate of the perfusion value as calculated during time window "B" calculate the perfusion during time window "C" by fitting the measured bead mean temperature vs. time data during time window "C" to Equation (4).

(4) using the calculation for perfusion in step 3, recalculate the thermal conductivity and diffusivity during time window "A" by fitting the measured bead heating power vs. time data during time window "A" to Equation (3);

(5) using such recalculations for intrinsic thermal conductivity and diffusivity, recalculate the estimate of perfusion during time window "B" by fitting the measured bead heating power vs. time data during time window "B" to Equation (3);

(6) using such intrinsic thermal conductivity and diffusivity values, and the calculated perfusion estimate recalculate the perfusion during time window "C" by fitting the measured bead mean temperature vs. time data during time window "C" to Equation (4);

(7) repeat stages (4), (5) and (6) until convergence to substantially non-changing thermal conductivity and diffusivity values and a substantially non-changing perfusion value is achieved.

Further refinement may be achieved in the above algorithm by making similar calculations between time windows "C" and "A" and then again between time windows "A" and "B", and again between time windows "B" and "C", and so forth, until the appropriate convergences occur, each subsequent recalculations providing further accuracy until an optimum accuracy is recorded. An alternative to the above scheme would be to perform iterative calculations, passing consecutively from time window "A" to time window "B" to time window "C" and back to time window "A", etc.

Figure 2:
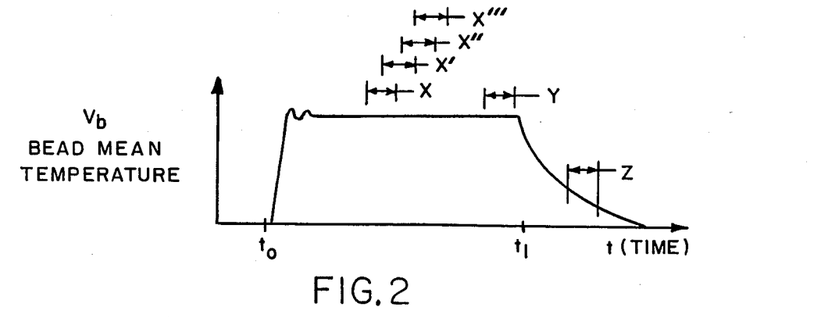
FIG. 2 depicts a curve of bead volume mean temperature as a function of time with reference to another embodiment of the invention.
Figure 3:
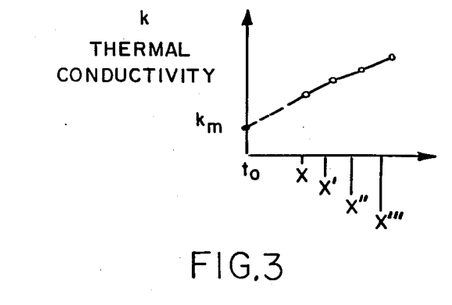
FIG. 3 depicts an extrapolated curve of thermal conductivity with reference to the embodiment of the invention referred to in connection with FIG. 2.
Figure 3A:
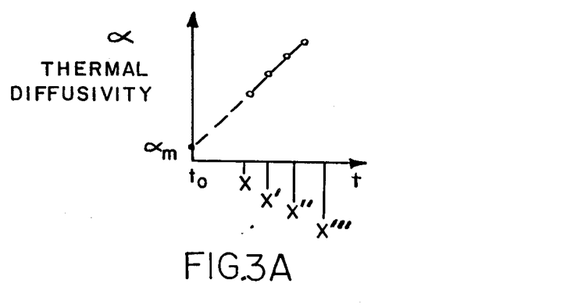
FIG. 3A depicts an extrapolated curve of thermal diffusivity as a function of time with reference to the embodiment of the invention referred to in connection with FIG. 2.

Another exemplary alternative algorithm usable at time windows "A" and "B" consists of the following steps:

(1) calculate a plurality of effective thermal conductivity and thermal diffusivity values during a plurality of time windows $X^i$ where $X^i$ is X, $X^1$, $X^{11}$, etc, such as depicted in FIG. 2, by fitting the measured bead heating power vs. time data during time window "$X^i$" to Equation (3), with an arbitrary value to perfusion e.g. assume perfusion equal to zero;

(2) extrapolate the thermal conductivity and diffusivity values obtained in step (1), above to time $t_o$, i.e., to the instant of time at which heating begins (See FIGS. 3 and 3A where the points X, $X^1$, $X^{11}$, etc. are selected at the same normalized position within each window, e.g. the middle or the end of each window). Such extrapolated values will equal, or nearly equal, the non-perfused, intrinsic thermal conductivity $k_m$ and the non-perfused, intrinsic thermal diffusivity $\alpha_m$.

(3) using such extrapolated values of intrinsic thermal conductivity and diffusivity, calculate the perfusion at a selected time during which a perfusion effect occurs, e.g. time window "Y" (FIG. 2) by fitting the measured bead heating power vs. time data during time window "Y" to Equation (3); or time window "Z" (FIG. 2) by fitting the measured bead volume mean temperature vs. time data during time window "Z" to Equation (4).

(4) recalculate the intrinsic thermal conductivity and diffusivity at said plurality of time windows $X^i$ of step (1) above, using the calculated perfusion value form the selected time window "Y" and/or "Z";

(5) extrapolate the thermal conductivity and diffusivity values obtained in step (4) to time $t_o$;

(6) recalculate the perfusion at the selected time window "Y" and/or "Z" using the extrapolated thermal conductivity and diffusivity values calculated in step (5);

(7) repeat steps (4), (5) and (6) until convergence to substantially non-changing intrinsic thermal conductivity and thermal diffusivity values and a substantially non-changing perfusion value is achieved.

The potential for improvement over the techniques of the previous Bowman patent offered by the combined heating/cooling experimental procedure, by the use of the above discussed enhanced mathematical model, and by the analysis procedures discussed above is significant. Measurement of perfusion levels below 10 ml/100 gm-min is now possible to an accuracy of ±10%, as compared to a lower limit of approximately 50–60 ml/100 gm-min to an accuracy of 10% with the earlier described approach. Since most tumor blood flow levels in human or animal tissue lie in the range of 0–40 ml/100 gm-min and skeletal muscle perfusion levels typically lie in the range of 2–20 ml/100 gm-min, the techniques of the invention now permit accurate data to be obtained for such conditions, which data it was not heretofore possible to obtain. In the previously described approach, two experiments were required, one at a flow condition and one at a no-flow condition. Accurate data at the latter condition was difficult to achieve at the same measurement site in tissues and increased considerably the uncertainty in the perfusion measurements made under flow conditions.

Moreover, no previous procedures have been known which did not require special conditions or extremely sensitive, complex and often relatively expensive instrumentation in which the data which is obtained is relative, rather than absolute, in nature, which data are often unsuitable for computational processing. The procedures of the invention now avoid the necessity for a no-flow experiment and are based on an improved mathematical model which permits the use of readily implemented computational processing for achieving improved measurement accuracy at much lower perfusion levels than previously possible.

While the above description of techniques for offering measurements of thermal conductivity, diffusivity and perfusion in media are directed to the use of a thermistor bead, or its equivalent, and applying power to heat the bead and, accordingly, to heat the medium, the invention is not limited thereto. For example, rather than applying heat to the medium in an internal or invasive sense by applying power to a bead or probe immersed therein, heat can be applied non-invasively to the medium from an external heat source. In such case, the basic thermal model will be such as to require the use only of the thermal model for the medium which would be analogous to Equation (2), additionally accounting for the non-invasive heating source. Suitable equations for use in accordance with the techniques of the invention then can be derived by those in the art for use under such conditions.

Further, while the above illustrative embodiments discuss procedures in which the temperature is raised to and maintained at a higher level for a finite time period, this analysis technique may also be applied to measurements obtained during an experiment wherein the temperature is raised to an appropriate level and held there for a very short time period (and even held only for an instant of time) and then allowed to relax to a final unperturbed value, the measurements desired also being taken at any suitable selected separate times during the overall time cycle.

Moreover, while the above techniques are based on the concept of raising the temperature of a medium (or of a bead which in turn raises that of the medium) and permitting the temperature subsequently to decay or relax to an unperturbed value, the general approach of the invention can be used when the medium (or bead, if appropriate) is cooled from an unperturbed first temperature to a second temperature which is lower than the first temperature and then is subsequently permitted to relax so as to rise its unperturbed temperature. Appropriate changes in the equations to be used in accordance with the invention can be made appropriately within the skill of those in the art.

While in all of the above cases the experimental duration is such that measurements are made over a relatively short time period such that the initial unperturbed temperature and subsequently final unperturbed temperature are subsequently equal, the medium in some instances may be subject to a general overall change in temperature due to other environmental causes (e.g. the overall temperature of the medium may be rising due to other causes at a steady rate during the overall recommended time period). In such cases, the final unperturbed temperature to which the medium relaxes after initial heating (or cooling) may be somewhat different from the initial unperturbed temperature at the initiation of heating (or cooling). By suitably monitoring the initial and final unperturbed temperatures, the calculations can be appropriately adjusted to take into account such general overall temperature changes which are due to other causes (e.g., baseline drift).

Other modifications to and variations in the concept of the invention may occur to those in the art within the spirit and scope of the invention. Hence, the invention is not to be deemed as limited to the particular embodiments described above, except as defined by the appended claims.

What is claimed is:

1. A method for determining properties of a medium comprising the steps of
   (1) causing the temperature of said medium to change from a first unperturbed temperature to a second temperature different from said first temperature during a first time period.
   (2) causing the temperature of said medium to relax to a final unperturbed temperature during a second time period.
   (3) calculating an intrinsic thermal conductivity and a diffusivity of said medium during a first selected portion of said first and second time periods;
   (4) calculating a perfusion of said medium at at least a second selected portion of said first and second time periods using said calculated intrinsic thermal conductivity and diffusivity;
   (5) re-calculating the intrinsic thermal conductivity and diffusivity of said medium during said first selected portion of said first and second time periods using said calculated perfusion;
   (6) re-calculating the perfusion of said medium at least at said second selected portion of said first and second time periods using said recalculated intrinsic thermal conductivity and diffusivity; and
   (7) repeating steps (5) and (6) until the re-calculated intrinsic thermal conductivity and diffusivity and the re-calculated perfusion each converge to a substantially non-changing value.

2. A method in accordance with claim 1 wherein step (1) includes
   immersing a temperature changing means in said medium; and
   activating said temperature chaning means so as to cause said means to change the temperature of said medium.

3. A method in accordance with claim 1 wherein step (1) includes
   immersing a cooling means in said medium; and
   applying power to said cooling means to cool said medium from said first unperturbed temperature; and
   said step (2) includes
   shutting off the power to said cooling means to cause the temperature of said medium to rise to said final unperturbed temperature during said second time period.

4. A method in accordance with claim 1 wherein in step (3) the intrinsic thermal conductivity and diffusivity are calculated at a first selected portion of said first time period.

5. A method in accordance with claim 4 wherein in step (4) the perfusion is calculated at a second selected portion of said first time period.

6. A method in accordance with claim 4 wherein in step (4) the perfusion is calculated at a second selected portion of said second time period.

7. A method in accordance with claim 1 wherein step (1) includes
   immersing a heating means in said medium;
   applying power to said heating means to heat said medium from said first unperturbed temperature to said second temperature;
   and step (2) includes
   shutting off the power to said heating means to cause the temperature of said medium to decay to said final unperturbed temperature during said second time period.

8. A method in accordance with claim 7 wherein said heating means has a substantially spherical configuration and said intrinsic thermal conductivity and diffusivity are calculated and recalculated in steps (3) and (5) and the perfusion is calculated and recalculated in steps (4) and (6) using the following equation (A) for the first time period and the following equation (B) for the second time period.:

$$P(t) = \frac{4\pi a k_m \Delta T}{\frac{1}{5\gamma} + \frac{1}{1 + \lambda a}} \left[ 1 + \frac{\frac{a}{\sqrt{\pi a_m}} f(t)}{\frac{1 - \lambda^2 a^2}{5\gamma} + 1 + \lambda a} \right] \quad (A)$$

$$V_b(t) = \Delta T$$

$$P(t) = 0$$

-continued $$\frac{V_b(t)}{\Delta T} = \frac{a/\sqrt{\pi\alpha_m}}{\frac{1-\lambda^2 a^2}{5\gamma} + 1 - \lambda a} \left[ \{f(t - t_{heat}) - f(t)\} + \frac{a/\sqrt{\pi\alpha_m}}{\frac{1-\lambda^2 a^2}{5\gamma} + 1 + \lambda a} \frac{\sqrt{t_{heat}}\, e^{-\lambda^2 \alpha_m t}}{t\sqrt{t - t_{heat}}} \right] \quad (B)$$

wherein P(t) is the power applied, a is the radius of the spherical heating means, $k_m$ and $\alpha_m$ are, respectively, the intrinsic thermal conductivity and thermal diffusivity of said medium, $\Gamma$ is the ratio $k_b/k_m$, $k_b$ is the intrinsic thermal conductivity of the spherical heating means, $\lambda$ is equal to $\sqrt{wc_m/k_m}$, where w is perfusion and $c_f$ is the specific heat of the perfusate, $V_b$ is the bead mean volumetric temperature during cooling, $\Delta T$ is the volume averaged constant temperature change during the heating phase, $t_{heat}$ is the length of time for which heating is applied and f(t) represents the temporal form of the transient power applied to said heating means as a function of time.

9. A method in accordance with claim 7 wherein said heating means has a substantially spherical configuration and said intrinsic thermal conductivity and diffusivity are calculated and recalculated in steps (3) and (5) and the perfusion is calculated and recalculated in steps (4) and (6) using the following equation (C) for the first time period and the following equation (D) for the second time period:

$$P = P_o$$

and $$V_b(t) = \frac{P_o}{4\pi a k_a} \left[ \frac{1}{5\gamma} + \frac{1}{1+\lambda a} - \frac{a/\sqrt{\pi\alpha_m}}{1-\lambda^2 a^2} f(t) \right] \quad (C)$$

$$P = 0$$

$$V_b(t) = \frac{P_o}{4\pi k_a \sqrt{\pi\alpha_m}} \frac{1}{1-\lambda^2 a^2} [f(t - t_{heat}) - f(t)] \quad (D)$$

wherein $P_o$ is the constant power applied during the heating phase, a is the radius of the spherical heating means, $k_m$ and $\alpha_m$ are, respectively, the intrinsic thermal conductivity and thermal diffusivity of said medium, $\gamma$ is the ratio $k_b/k_m$, $k_b$ is the intrinsic thermal conductivity of the spherical heating means, $\lambda$ is equal to $\sqrt{wc_m/k_m}$, where w is perfusion and $c_f$ is the specific heat of the perfusate, $V_b$ is the bead man volumetric temperature during cooling, $t_{heat}$ is the length of time for which heating is applicated and f(t) represents the temporal form of the transient power applied to said heating means as a function of time.

10. A method for determining properties of a medium comprising the steps of
   (1) causing the temperature of said medium to change from a first unperturbed temperature to a second temperature different from said first temperature during an overall time period;
   (2) calculating effective thermal conductivity and diffusivity values of said medium during a plurality of time periods within said overall time period;
   (3) extrapolating the effective thermal conductivity and diffusivity values calculated in step (2) to the thermal conductivity and diffusivity values at a selected time $t_o$ when the temperature of said medium is first caused to change so as to determine the extrapolated values of the intrinsic thermal conductivity and diffusivity of said medium;
   (4) calculating a perfusion of said medium during a selected time period of said overall time period using said extrapolated intrinsic thermal conductivity and diffusivity;
   (5) recalculating the effective thermal conductivity and diffusivity values of said medium during said plurality of time periods; using said calculated perfusion;
   (6) re-extrapolating the thermal conductivity and diffusivity values recalculated in step (5) to the intrinsic thermal conductivity and diffusivity values at said selected time $t_o$;
   (7) recalculating the perfusion of said medium during said selected time period using the intrinsic thermal conductivity and diffusivity values reextrapolated in step (6); and
   (8) repeating steps (5) through (7) until the recalculated intrinsic thermal conductivity and diffusivity values and the recalculated perfusion value converge to substantially non-changing values.

11. A method in accordance with claim 10 wherein the temperature change produced in said medium is constant and further wherein in steps (2) and (5) the thermal conductivity and diffusivity are calculated in accordance with the following equation:

$$P(t) = \frac{4\pi a k_a \Delta T}{\frac{1}{5\gamma} + \frac{1}{1+\lambda a}} \left[ 1 + \frac{\frac{a}{\sqrt{\pi\alpha_a}} f(t)}{\frac{1-\lambda^2 a^2}{5\gamma} + 1 + \lambda a} \right].$$

12. A method in accordance with claim 10 wherein the temperature change produced in said medium is constant and further wherein in steps (4) and (7) the perfusion is calculated in accordance with the following equation:

$$P(t) = \frac{4\pi a k_a \Delta T}{\frac{1}{5\gamma} + \frac{1}{1+\lambda a}} \left[ 1 + \frac{\frac{a}{\sqrt{\pi\alpha_a}} f(t)}{\frac{1-\lambda^2 a^2}{5\gamma} + 1 + \lambda a} \right].$$

13. A method in accordance with claim 10 wherein the temperature change produced in said medium is constant and further wherein in step (4) and (7) the perfusion is calculated in accordance with the following equation, for a time period which is subsequent to the deactivation of the temperature changing means:

$$\frac{V_b(t)}{\Delta T} = \frac{a/\sqrt{\pi \alpha_m}}{\frac{1-\lambda^2 a^2}{5\gamma} + 1 - \lambda a} \left[ \frac{\{f(t - t_{heat}) - f(t)\} +}{\frac{a/\sqrt{\pi \alpha_m}}{\frac{1-\lambda^2 a^2}{5\gamma} + 1 + \lambda a}} \frac{\sqrt{t_{heat}}\, e^{-\lambda^2 \alpha_m t}}{t\sqrt{t - t_{heat}}} \right].$$

14. A method in accordance with claim 10 wherein the temperature change in said medium is produced by activating a power source so as to produce a change in power which is constant and further wherein in steps (2) and (5) the thermal conductivity and diffusivity are calculated in accordance with the following equation:

$$V_b(t) = \frac{P_0}{4\pi a k_a}\left[ \frac{1}{5\gamma} + \frac{1}{1+\lambda a} - \frac{a/\sqrt{\pi \alpha_m}}{1-\lambda^2 a^2} f(t) \right].$$

15. A method in accordance with claim 10 wherein the tamperature change in said medium is produced by activating a power source so as to produce a change in power which is constant and further wherein in steps (4) and (7) the perfusion is calculated in accordance with the following equation:

$$V_b(t) = \frac{P_0}{4\pi a k_a}\left[ \frac{1}{5\gamma} + \frac{1}{1+\lambda a} - \frac{a/\sqrt{\pi \alpha_m}}{1-\lambda^2 a^2} f(t) \right].$$

16. A method in accordance with claim 10 wherein the temperature change in said medium is produced by activating a power source so as to produce a change in power which is constant and further wherein in steps (4) and (7) the perfusion is calculated in accordance with the following equation, for a time period which is subsequent to the deactivation of the power source:

$$V_b(t) = \frac{P_o}{4\pi k_a \sqrt{\pi \alpha_m}} \frac{1}{1-\lambda^2 a^2}[f(t-t_{heat}) - f(t)].$$

17. A method for determining properties of a medium comprising the steps of
  causing the temperature of the medium to change in any arbitrarily selected manner as a function of time:
  calculating at least one selected intrinsic thermal property of said medium using data obtained at a first time period; and
  calculating separately a perfusion of said medium using data obtained at a second time period and said at least one calculated intrinsic thermal property, the effects of the flow of said medium at said second time period being greater than the effects of the flow of said medium at said first time period.

* * * * *